(12) United States Patent
Blier (10) Patent No.: US 8,025,640 B2
(45) Date of Patent: Sep. 27, 2011

(54) PRESSURIZED SURGICAL VALVE

(75) Inventor: Kenneth Blier, Meriden, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 64 days.

(21) Appl. No.: 12/476,365

(22) Filed: Jun. 2, 2009

(65) Prior Publication Data

US 2009/0326468 A1    Dec. 31, 2009

Related U.S. Application Data (60) Provisional application No. 61/076,190, filed on Jun. 27, 2008.

(51) Int. Cl.
*A61M 5/178* (2006.01)
(52) U.S. Cl. .................................. 604/167.01
(58) Field of Classification Search .............. 604/164.01
See application file for complete search history.

(56) References Cited

U.S. PATENT DOCUMENTS

| | | |
|---|---|---|
| 1,690,995 A | 12/1927 | Pratt |
| 2,319,554 A | 11/1940 | Penn et al. |
| 3,834,546 A | 9/1974 | Brun et al. |
| 3,970,089 A | 7/1976 | Saice |
| 4,177,814 A | 12/1979 | Knepshield et al. |
| 4,555,242 A | 11/1985 | Saudagar |
| 4,610,665 A | 9/1986 | Matsumoto et al. |
| 4,637,396 A | 1/1987 | Cook |
| 4,655,752 A | 4/1987 | Honkanen et al. |
| 4,738,666 A | 4/1988 | Fuqua |
| 4,760,933 A | 8/1988 | Christner et al. |
| 4,796,629 A | 1/1989 | Grayzel |
| 4,828,554 A | 5/1989 | Griffin |
| 4,890,612 A | 1/1990 | Kensey |
| 4,909,798 A | 3/1990 | Fleischhacker et al. |
| 4,978,341 A | 12/1990 | Niederhauser |
| 5,002,557 A | 3/1991 | Hasson |
| 5,071,411 A | 12/1991 | Hillstead |
| 5,127,626 A | 7/1992 | Hilal et al. |
| 5,158,553 A | 10/1992 | Berry et al. |
| 5,197,955 A | 3/1993 | Stephens et al. |
| 5,201,714 A | 4/1993 | Gentelia et al. |
| 5,209,736 A | 5/1993 | Stephens et al. |
| 5,209,737 A | 5/1993 | Ritchart et al. |
| 5,211,633 A | 5/1993 | Stouder, Jr. |

(Continued)

FOREIGN PATENT DOCUMENTS

EP    336903    11/1989

(Continued)

OTHER PUBLICATIONS

European Search Report, Application No. EP 09 25 1638 dated Oct. 13, 2009.

(Continued)

*Primary Examiner* — Nicholas D Lucchesi
*Assistant Examiner* — Jason Flick (57) ABSTRACT

A surgical access assembly for use during the course of a minimally invasive procedure includes a pump assembly to selectively communicate to and from the seal member such that the seal may transition from a first condition to at least one subsequent condition. In the first condition, the seal member is configured to allow a surgical object to pass therethrough with little resistance, and in the at least one subsequent condition, the seal member forms a substantially fluid tight seal with the surgical object.

19 Claims, 8 Drawing Sheets

U.S. PATENT DOCUMENTS

| | | | |
|---|---|---|---|
| 5,226,890 A | 7/1993 | Ianniruberto et al. | |
| 5,242,412 A | 9/1993 | Blake, III | |
| 5,266,880 A | 11/1993 | Newland | |
| 5,273,545 A | 12/1993 | Hunt et al. | |
| 5,308,336 A | 5/1994 | Hart et al. | |
| 5,330,437 A | 7/1994 | Durman | |
| 5,331,975 A | 7/1994 | Bonutti | |
| 5,350,364 A | 9/1994 | Stephens et al. | |
| 5,360,417 A | 11/1994 | Gravener et al. | |
| 5,364,372 A | 11/1994 | Danks et al. | |
| 5,366,478 A | 11/1994 | Brinkerhoff et al. | |
| 5,380,288 A | 1/1995 | Hart et al. | |
| 5,385,553 A | 1/1995 | Hart et al. | |
| RE34,866 E | 2/1995 | Kensey et al. | |
| 5,389,080 A | 2/1995 | Yoon | |
| 5,391,156 A | 2/1995 | Hildwein et al. | |
| 5,403,336 A | 4/1995 | Kieturakis et al. | |
| 5,407,433 A | 4/1995 | Loomas | |
| 5,411,483 A | 5/1995 | Loomas et al. | |
| 5,413,571 A | 5/1995 | Katsaros et al. | |
| 5,429,609 A | 7/1995 | Yoon | |
| 5,441,486 A | 8/1995 | Yoon | |
| 5,460,616 A | 10/1995 | Weinstein et al. | |
| 5,468,248 A | 11/1995 | Chin et al. | |
| 5,476,475 A | 12/1995 | Gadberry | |
| 5,478,318 A | 12/1995 | Yoon | |
| 5,480,410 A | 1/1996 | Cuschieri et al. | |
| 5,496,280 A | 3/1996 | Vandenbroek et al. | |
| 5,509,888 A | 4/1996 | Miller | |
| 5,514,109 A | 5/1996 | Mollenauer et al. | |
| 5,514,133 A | 5/1996 | Golub et al. | |
| 5,531,758 A | 7/1996 | Uschold et al. | |
| 5,538,509 A | 7/1996 | Dunlap et al. | |
| 5,540,711 A | 7/1996 | Kieturakis et al. | |
| 5,545,142 A | 8/1996 | Stephens et al. | |
| 5,545,150 A | 8/1996 | Danks et al. | |
| 5,545,179 A | 8/1996 | Williamson, IV | |
| 5,580,344 A | 12/1996 | Hasson | |
| 5,584,850 A | 12/1996 | Hart et al. | |
| 5,607,443 A | 3/1997 | Kieturakis et al. | |
| 5,634,911 A | 6/1997 | Hermann et al. | |
| 5,634,937 A | 6/1997 | Mollenauer et al. | |
| 5,636,645 A | 6/1997 | Ou | |
| 5,640,977 A | 6/1997 | Leahy et al. | |
| 5,643,911 A | 7/1997 | Yamada et al. | |
| 5,653,705 A | 8/1997 | De la Torre et al. | |
| 5,662,615 A | 9/1997 | Blake, III | |
| 5,672,168 A | 9/1997 | De la Torre et al. | |
| 5,679,266 A | 10/1997 | Darekar et al. | |
| 5,709,664 A | 1/1998 | Vandenbroek et al. | |
| 5,720,730 A | 2/1998 | Blake, III | |
| 5,727,770 A | 3/1998 | Dennis | |
| 5,743,884 A | 4/1998 | Hasson et al. | |
| 5,752,970 A | 5/1998 | Yoon | |
| 5,779,624 A | 7/1998 | Chang | |
| 5,779,697 A | 7/1998 | Glowa et al. | |
| 5,782,817 A | 7/1998 | Franzel et al. | |
| 5,788,676 A | 8/1998 | Yoon | |
| 5,792,113 A | 8/1998 | Kramer et al. | |
| 5,797,888 A | 8/1998 | Yoon | |
| 5,803,921 A | 9/1998 | Bonadio | |
| 5,813,409 A | 9/1998 | Leahy et al. | |
| 5,814,026 A | 9/1998 | Yoon | |
| 5,842,971 A | 12/1998 | Yoon | |
| 5,853,395 A | 12/1998 | Crook et al. | |
| 5,853,995 A | 12/1998 | Lee | |
| 5,865,807 A | 2/1999 | Blake, III | |
| 5,871,474 A | 2/1999 | Hermann et al. | |
| 5,882,345 A | 3/1999 | Yoon | |
| 5,906,577 A | 5/1999 | Beane et al. | |
| 5,906,595 A | 5/1999 | Powell et al. | |
| 5,913,847 A | 6/1999 | Yoon | |
| 5,916,198 A | 6/1999 | Dillow | |
| 5,925,064 A | 7/1999 | Meyers et al. | |
| 5,950,779 A | 9/1999 | Miyoshi | |
| 5,957,898 A | 9/1999 | Jepson et al. | |
| 5,957,913 A | 9/1999 | De la Torre et al. | |
| 5,964,781 A | 10/1999 | Mollenauer et al. | |
| 5,989,224 A | 11/1999 | Exline et al. | |
| 5,989,232 A | 11/1999 | Yoon | |
| 5,989,233 A | 11/1999 | Yoon | |
| 5,993,471 A | 11/1999 | Riza et al. | |
| 6,004,303 A | 12/1999 | Peterson | |
| 6,010,494 A | 1/2000 | Schafer et al. | |
| 6,024,736 A | 2/2000 | De la Torre et al. | |
| 6,042,573 A * | 3/2000 | Lucey | 604/246 |
| 6,045,535 A | 4/2000 | Ben Nun | |
| 6,071,265 A | 6/2000 | Bestetti et al. | |
| 6,083,203 A | 7/2000 | Yoon | |
| 6,123,689 A | 9/2000 | To et al. | |
| 6,135,660 A | 10/2000 | Stevens et al. | |
| 6,142,936 A | 11/2000 | Beane et al. | |
| 6,152,933 A | 11/2000 | Werp et al. | |
| 6,159,200 A | 12/2000 | Verdura et al. | |
| 6,165,184 A | 12/2000 | Verdura et al. | |
| 6,197,002 B1 | 3/2001 | Peterson | |
| 6,203,526 B1 | 3/2001 | McBeth et al. | |
| 6,221,050 B1 | 4/2001 | Ishida | |
| 6,221,057 B1 | 4/2001 | Schwartz et al. | |
| 6,228,068 B1 | 5/2001 | Yoon | |
| 6,231,553 B1 | 5/2001 | Hulett | |
| 6,238,373 B1 | 5/2001 | De la Torre et al. | |
| 6,258,065 B1 | 7/2001 | Dennis et al. | |
| 6,260,616 B1 | 7/2001 | Carmody et al. | |
| 6,261,282 B1 | 7/2001 | Jepson et al. | |
| 6,276,661 B1 | 8/2001 | Laird | |
| 6,302,866 B1 | 10/2001 | Marggi | |
| 6,315,770 B1 | 11/2001 | De la Torre et al. | |
| 6,319,246 B1 | 11/2001 | De la Torre et al. | |
| 6,334,486 B1 | 1/2002 | Carmody et al. | |
| 6,344,033 B1 | 2/2002 | Jepson et al. | |
| 6,358,266 B1 | 3/2002 | Bonutti | |
| 6,413,244 B1 | 7/2002 | Bestetti | |
| 6,416,504 B2 | 7/2002 | Mosel et al. | |
| 6,440,063 B1 | 8/2002 | Beane et al. | |
| 6,447,489 B1 | 9/2002 | Peterson | |
| 6,450,255 B2 | 9/2002 | Carmody et al. | |
| 6,450,983 B1 | 9/2002 | Rambo | |
| 6,461,332 B1 | 10/2002 | Mosel et al. | |
| 6,468,292 B1 | 10/2002 | Mollenauer et al. | |
| 6,484,800 B2 | 11/2002 | Carmody et al. | |
| 6,485,467 B1 | 11/2002 | Crook et al. | |
| 6,551,270 B1 | 4/2003 | Bimbo et al. | |
| 6,551,282 B1 | 4/2003 | Exline et al. | |
| 6,570,738 B1 | 5/2003 | McKinstry | |
| 6,578,577 B2 | 6/2003 | Bonadio et al. | |
| 6,582,364 B2 | 6/2003 | Butler et al. | |
| 6,595,946 B1 | 7/2003 | Pasqualucci | |
| 6,612,547 B2 | 9/2003 | Carmody et al. | |
| 6,613,952 B2 | 9/2003 | Rambo | |
| 6,620,138 B1 | 9/2003 | Marrgi et al. | |
| 6,623,426 B2 | 9/2003 | Bonadio et al. | |
| 6,629,530 B2 | 10/2003 | Cise | |
| 6,663,598 B1 | 12/2003 | Carrillo, Jr. et al. | |
| 6,669,674 B1 | 12/2003 | Macoviak et al. | |
| 6,669,681 B2 | 12/2003 | Jepson et al. | |
| 6,723,088 B2 | 4/2004 | Gaskill, III et al. | |
| 6,743,165 B2 | 6/2004 | Mosel et al. | |
| 6,810,880 B1 | 11/2004 | Jennings, Jr. et al. | |
| 6,840,951 B2 | 1/2005 | De la Torre et al. | |
| 6,846,287 B2 | 1/2005 | Bandio et al. | |
| 6,863,661 B2 | 3/2005 | Carrillo, Jr. et al. | |
| 6,890,330 B2 | 5/2005 | Streeter et al. | |
| 6,923,783 B2 | 8/2005 | Pasqualucci | |
| 6,942,671 B1 | 9/2005 | Smith | |
| 6,942,672 B2 | 9/2005 | Heilman et al. | |
| 6,945,933 B2 | 9/2005 | Branch et al. | |
| 6,949,084 B2 | 9/2005 | Marggi et al. | |
| 6,958,069 B2 | 10/2005 | Ship et al. | |
| 6,972,026 B1 | 12/2005 | Caldwell et al. | |
| 7,008,377 B2 | 3/2006 | Beane et al. | |
| 7,011,314 B2 | 3/2006 | McFarlane | |
| 7,033,339 B1 | 4/2006 | Lynn | |
| 7,052,454 B2 | 5/2006 | Taylor | |
| 7,081,089 B2 | 7/2006 | Bonadio et al. | |
| 7,105,009 B2 | 9/2006 | Johnson et al. | |
| 7,153,261 B2 | 12/2006 | Wenchell | |

| | | |
|---|---|---|
| 7,163,510 B2 | 1/2007 | Kahle et al. |
| 7,169,130 B2 | 1/2007 | Exline et al. |
| 7,195,590 B2 | 3/2007 | Butler et al. |
| 7,195,592 B2 | 3/2007 | Ravikumar et al. |
| 7,214,185 B1 | 5/2007 | Rosney et al. |
| 7,235,062 B2 | 6/2007 | Brustad |
| 7,235,084 B2 | 6/2007 | Skakoon et al. |
| 7,238,154 B2 | 7/2007 | Ewers et al. |
| 7,241,276 B2 | 7/2007 | Argentine et al. |
| 7,261,688 B2 | 8/2007 | Smith et al. |
| 7,297,106 B2 | 11/2007 | Yamada et al. |
| 7,300,399 B2 | 11/2007 | Bonadio et al. |
| 7,326,197 B2 | 2/2008 | Breznock et al. |
| 7,344,495 B2 | 3/2008 | Ravikumar et al. |
| 7,344,547 B2 | 3/2008 | Piskun |
| 7,377,898 B2 | 5/2008 | Ewers et al. |
| 7,390,316 B2 | 6/2008 | McFarlane |
| 7,390,317 B2 | 6/2008 | Taylor et al. |
| 7,393,322 B2 | 7/2008 | Wenchell |
| 7,434,325 B2 | 10/2008 | Foley et al. |
| 7,445,597 B2 | 11/2008 | Butler et al. |
| 7,445,623 B2 | 11/2008 | Mialhe |
| 7,470,261 B2 | 12/2008 | Lynn |
| 7,473,221 B2 | 1/2009 | Ewers et al. |
| 7,473,222 B2 | 1/2009 | Dewey et al. |
| 7,481,765 B2 | 1/2009 | Ewers et al. |
| 7,497,863 B2 | 3/2009 | Solar et al. |
| 7,513,869 B2 | 4/2009 | Branch et al. |
| 7,524,285 B2 | 4/2009 | Branch et al. |
| 7,537,564 B2 | 5/2009 | Bonadio et al. |
| 7,537,583 B2 | 5/2009 | Carrillo et al. |
| 7,540,839 B2 | 6/2009 | Butler et al. |
| 7,559,893 B2 | 7/2009 | Bonadio et al. |
| 7,559,918 B2 | 7/2009 | Pasqualucci |
| 7,559,935 B2 | 7/2009 | Solar et al. |
| 7,582,071 B2 | 9/2009 | Wenchell |
| 7,608,082 B2 | 10/2009 | Cuevas et al. |
| 2002/0183594 A1 | 12/2002 | Beane et al. |
| 2002/0188319 A1 | 12/2002 | Morris et al. |
| 2003/0019554 A1 | 1/2003 | Agostini et al. |
| 2007/0265502 A1 * | 11/2007 | Minosawa et al. ............ 600/173 |
| 2008/0269696 A1 | 10/2008 | Exline et al. |

FOREIGN PATENT DOCUMENTS

| | | |
|---|---|---|
| EP | 0674879 | 3/1995 |
| EP | 1681030 | 7/2006 |
| EP | 2050403 | 4/2009 |
| GB | 1024410 | 3/1966 |
| WO | WO 9422357 | 10/1994 |
| WO | WO 9507056 | 3/1995 |
| WO | WO 9522289 | 8/1995 |
| WO | WO 9527445 | 10/1995 |
| WO | WO 9527468 | 10/1995 |
| WO | WO 98/48724 | 11/1998 |
| WO | WO 9929250 | 6/1999 |
| WO | WO 9942152 | 8/1999 |
| WO | WO 03015848 | 2/2003 |
| WO | WO 2009058308 | 5/2009 |

OTHER PUBLICATIONS

Europen Search Report, Application No. EP 09 25 1615 dated Oct. 16, 2009.

* cited by examiner

PRESSURIZED SURGICAL VALVE

CROSS REFERENCE TO RELATED APPLICATION

The present application claims the benefit of and priority to U.S. Provisional Application Ser. No. 61/076,190, filed on Jun. 27, 2008, the entire contents of which are incorporated herein by reference.

BACKGROUND

1. Technical Field

The present disclosure relates to a surgical access assembly which is configured for removable insertion into a patient's tissue and the sealed reception of a surgical object.

2. Background of the Related Art

Many surgical procedures are performed through access devices such as trocar and cannula assemblies. These devices incorporate narrow tubes or cannulae percutaneously inserted into a patient's body, through which one or more surgical objects may be introduced and manipulated during the course of the procedure. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

Generally, during minimally invasive procedures, prior to the introduction of a surgical object into the patient's body, insufflation gases are used to enlarge the area surrounding the target surgical site to create a larger, more accessible work space. Accordingly, the maintenance of a substantially fluid-tight seal along the central opening of the access device in the presence of the surgical object is desirable. To this end, surgical access devices generally incorporate a seal through which the surgical object is inserted. The seal receives the surgical object in substantially sealed relation so as to prevent the escape of the insufflation gases and the deflation or collapse of the enlarged surgical work space. Examples of such seals may be seen through reference to commonly assigned U.S. Pat. No. 5,512,053 to Pearson and Provisional U.S. Patent Application Ser. No. 61/043,797 to Mozdzier et al., the entire contents of which are incorporated by reference herein.

During the course of a minimally invasive procedure, a clinician will frequently move surgical instruments laterally within the access assembly, and the seal, to access different regions of the surgical site. This lateral movement may cause the valve to stretch and deform, thereby causing the leakage of insufflation gas around the instrument. In addition, during the course of a typical procedure, a clinical will often interchange instrumentation of various sizes and diameters.

While many varieties of seals are known in the art, there exists a continuing need for a seal that can accommodate both the lateral movement of an instrument inserted therethrough, as well as differently sized instruments, while maintaining the integrity of an insufflated workspace.

SUMMARY

In one aspect of the present disclosure, a surgical access assembly is disclosed that includes a housing, an elongate access member, a seal member, and a pump assembly. The elongate access member extends distally from the housing and is dimensioned for positioning within a patient's tissue. The elongate access member defines a passageway extending therethrough that is configured to removably receive a surgical object.

The seal member has an aperture defined therein and extending therethrough. The seal member is adapted to transition between a first condition, in which the aperture includes a first transverse dimension that facilitates insertion of the surgical object, and at least one subsequent condition, in which the aperture includes a second, smaller transverse dimension that substantially approximates an outer dimension of a surgical object inserted through the aperture such that a substantially fluid-tight seal is formed therewith. The at least one subsequent condition may include a plurality of conditions in which the aperture defines an increasingly restricted transverse dimension. The seal member may be at least partially formed of a semi-resilient material that resiliently transitions between the first condition and the at least one subsequent condition upon activation of the pump assembly.

The seal member may include at least one egress in operative communication with the pump assembly which is configured to permit circulation of a fluid into and out of the seal member. In one embodiment, the seal member includes an internal cavity defined therein that is adapted to retain the fluid circulated throughout the seal member. However, in an alternate embodiment, the seal member includes a plurality of bladder members disposed within the internal cavity that are each adapted to retain the fluid therein. In this embodiment, each of the plurality of bladders resides in fluid communication with one another such that the fluid is circulated therebetween.

The pump assembly includes at least one pump member and is operatively coupled to the seal member. The pump assembly is selectively activatable between an activated state, in which the pump member circulates fluid into and out of the seal member, and a deactivated state to thereby facilitate the transition between the first condition and the at least one subsequent condition. The pump member includes a repositionable switch to transition the pump member between its activated and deactivated states.

In one embodiment, the pump assembly further includes a pressure transducer operatively coupled to the pump member. The pressure transducer is disposed between the seal member and the pump member and is configured to measure pressure exerted by the fluid within the seal member. The pressure transducer is adapted to translate the measured pressure into a first signal.

The pump assembly may further include a processing unit operably coupled to the pressure transducer. The processing unit is configured to receive and process the first signal into at least one additional signal to control the pump member.

In another embodiment, the pump assembly further includes at least one sensor operably coupled to the housing that are in communication with the processing unit. The sensor is adapted to detect at least one attribute of a surgical object, e.g., an outer dimension, color, electrical impedance, or magnetic impedance thereof, upon the introduction of the surgical object into the surgical access assembly. The sensor is configured to generate a signal in response to the detection of the surgical object to control the pump member.

In another aspect of the present disclosure, a method of performing a minimally invasive surgical procedure is disclosed that includes the steps of providing a surgical access assembly, inserting the surgical access assembly into a percutaneous access point formed in tissue, introducing at least one surgical object into the surgical access assembly, and activating a pump assembly.

The surgical access assembly includes a housing, an elongate access member, a seal member, and the pump assembly.

The elongate access member extends from the housing defining a lumen therethrough that is configured to removably receive the at least one surgical object.

The seal member is disposed within the housing and has an aperture defined therein and extending therethrough. The seal member is adapted to transition between a first condition, in which the aperture includes a first transverse dimension, and at least one subsequent condition, in which the aperture includes a second, smaller transverse dimension.

The pump assembly is operably coupled to the seal member and is configured to circulate into and out of the seal member to thereby respectively transition the seal member between the first condition and the at least one subsequent condition.

The step of activating the pump assembly facilitates the transition of the seal member from the first condition to the at least one subsequent condition to sealingly engage the surgical object therein.

These and other features of the valve disclosed herein will become more readily apparent to those skilled in the art from the following detailed description of various embodiments of the present disclosure.

BRIEF DESCRIPTION OF THE DRAWINGS

Various embodiments of the present disclosure are described herein below with references to the drawings, wherein.

DETAILED DESCRIPTION OF THE EMBODIMENTS

In the drawings and in the description which follows, in which like references numerals identify similar or identical elements, the term "proximal" will refer to the end of the apparatus which is closest to the clinician, while the term "distal" will refer to the end which is furthest from the clinician, as is traditional and known in the art. Additionally, use of the term "surgical object" herein below should be understood to include any surgical object or instrument that may be employed during the course of surgical procedure, including but not being limited to an obturator, a surgical stapling device, or the like.

Figure 1:
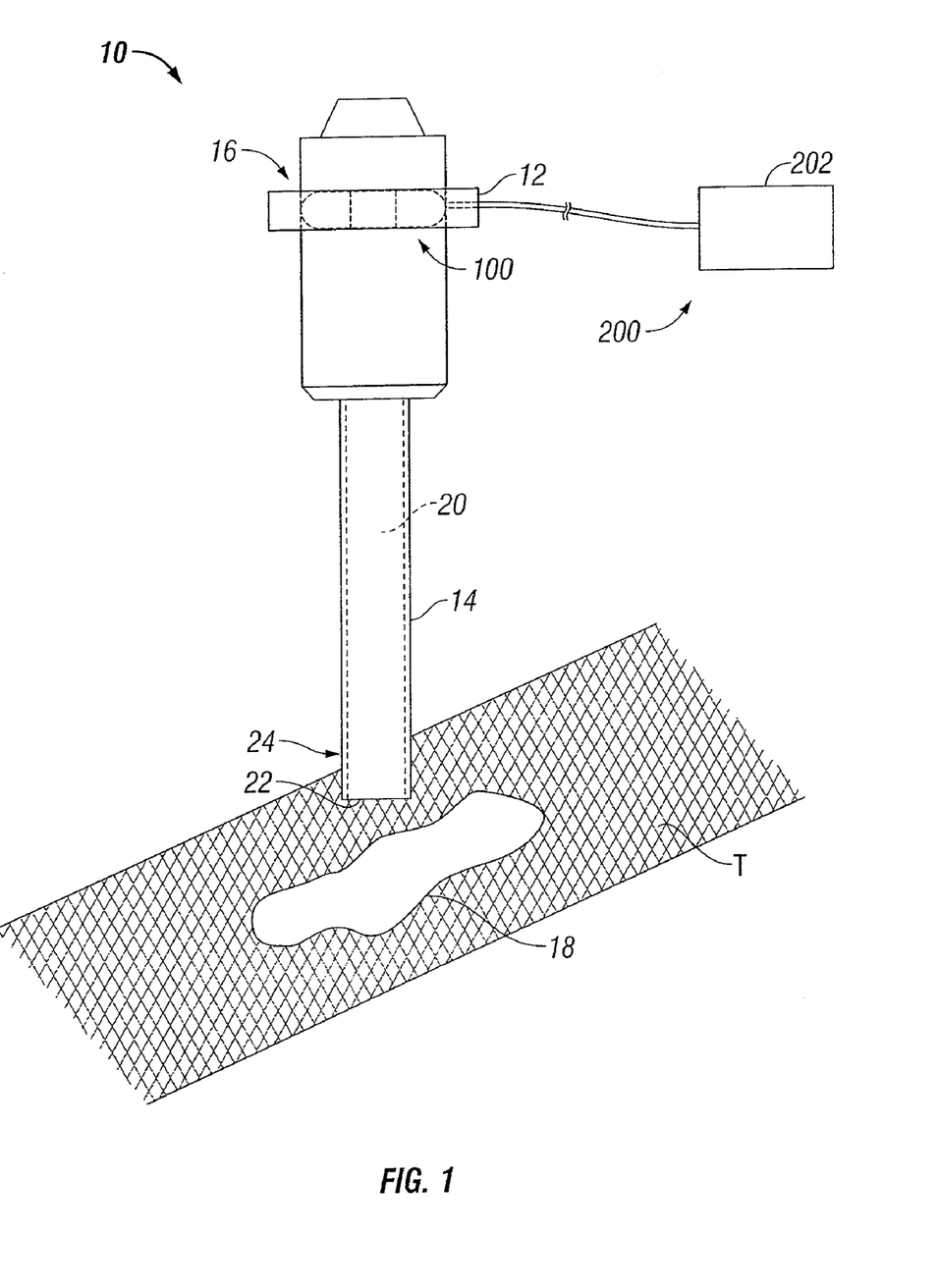
FIG. 1 is a side, schematic view of a surgical access assembly in accordance with the principles of the present disclosure including a seal member operatively associated with a pump assembly.

With reference to FIG. 1, a surgical access assembly 10 is depicted which includes a housing 12, a seal member 100, an elongate access member 14, and a pump assembly 200.

Housing 12 is disposed at a proximal end 16 of access assembly 10 and may be any structure suitable for the intended purpose of accommodating seal member 100. As is conventional in the art, housing 12 may include an insufflation port (not shown) to direct insufflation gas distally through access member 14 and into the body of a patient. Further information regarding valve housing 12 may be obtained through reference to commonly owned U.S. Pat. No. 7,169,130 to Exline et al., the entire contents of which are incorporated by reference herein.

Access member 14 extends distally from housing 12 and is dimensioned for positioning with a percutaneous access point 18, either pre-existing or created by a clinician, formed in a patient's tissue "T". Access member 14 defines a passageway 20 that extends therethrough along a longitudinal axis A-A. Passageway 20 is configured for the internal receipt of one or more surgical objects (not shown) and defines an opening 22 at the distal end 24 thereof dimensioned to allow the surgical objects to pass therethrough.

Figure 2A:
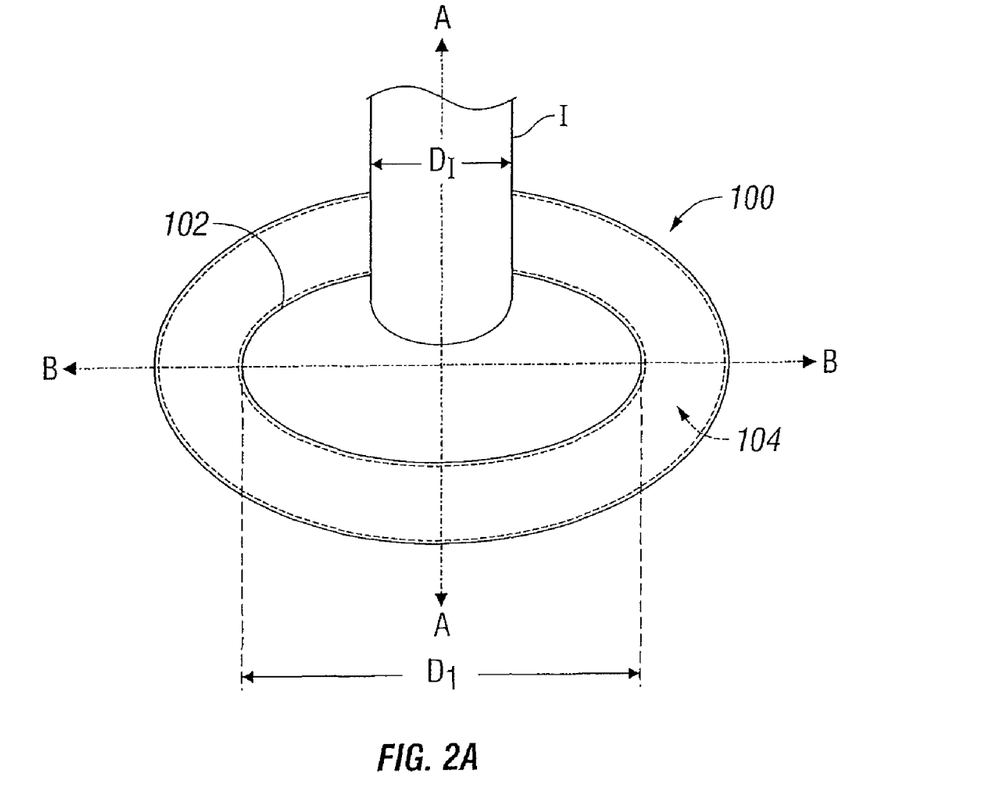
FIG. 2A is a top, schematic view of the seal member of FIG. 1 shown in a first condition prior to the insertion of a surgical object therethrough.
Figure 2B:
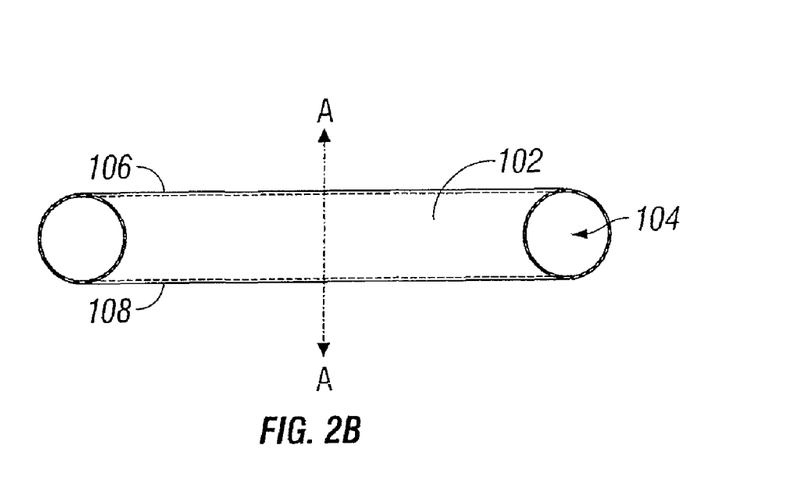
FIG. 2B is a side, cross-sectional view of the seal member of FIG. 2A shown in the first condition.
Figure 3A:
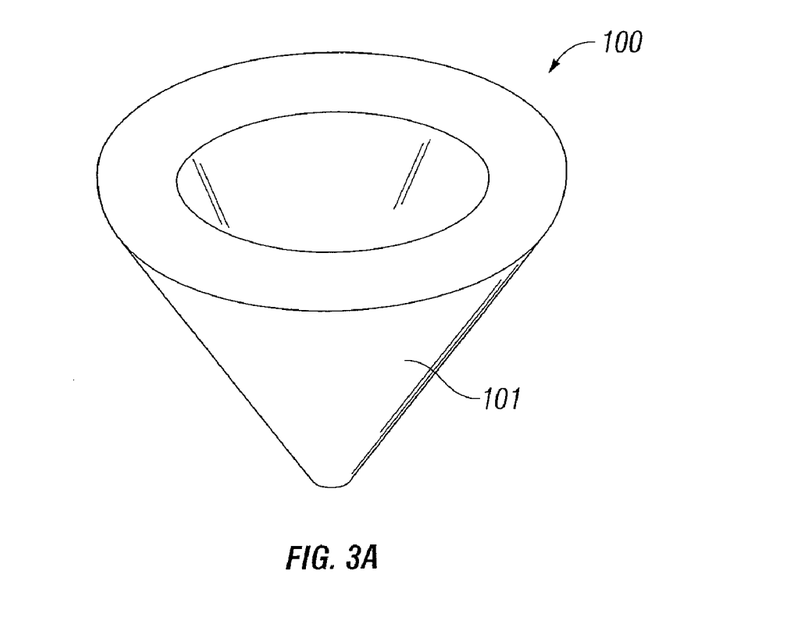
FIG. 3A is a top, perspective view of one embodiment of the valve of FIG. 1 having a substantially conical configuration.
Figure 3B:
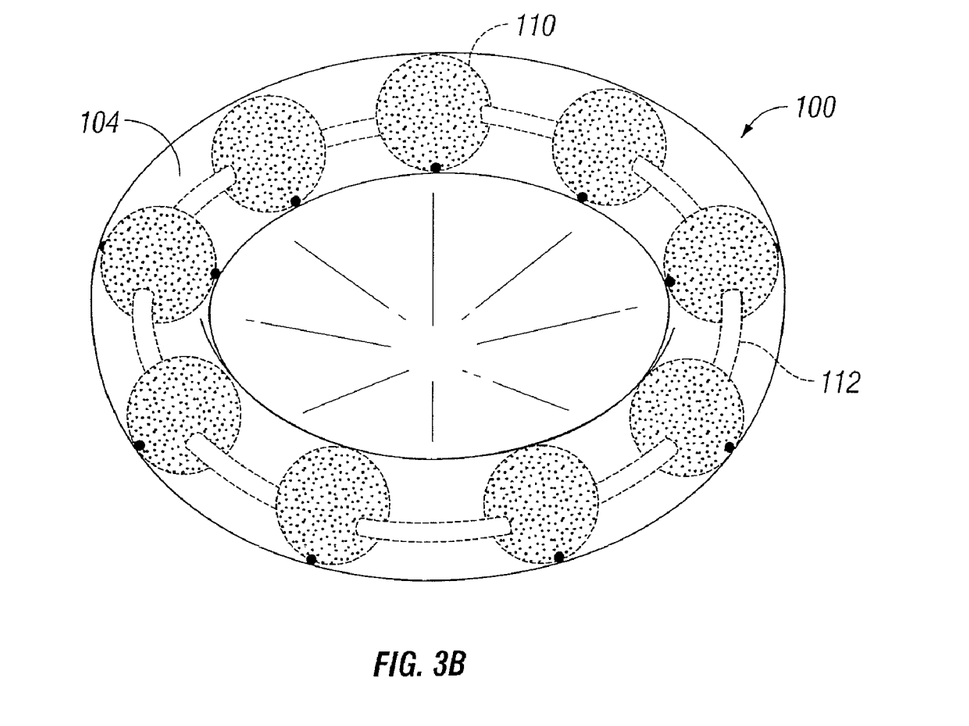
FIG. 3B is a top, schematic view of another embodiment of the valve of FIG. 1 including a plurality of inflatable bladder members.
Figure 4A:
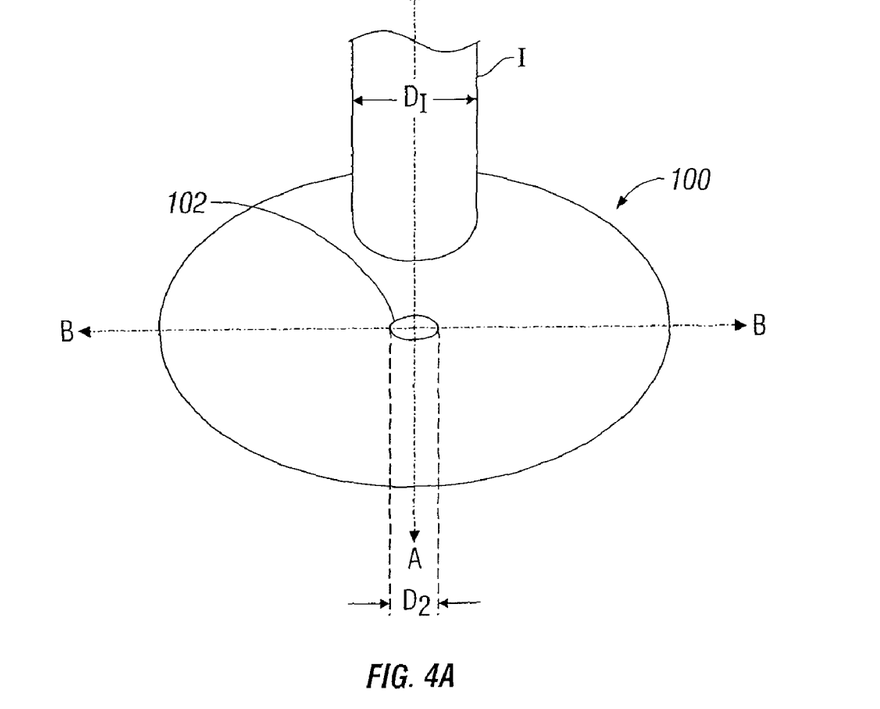
FIG. 4A is a top, schematic view of the seal member of FIG. 1 shown in a subsequent condition after to the insertion of a surgical object therethrough.
Figure 4B:
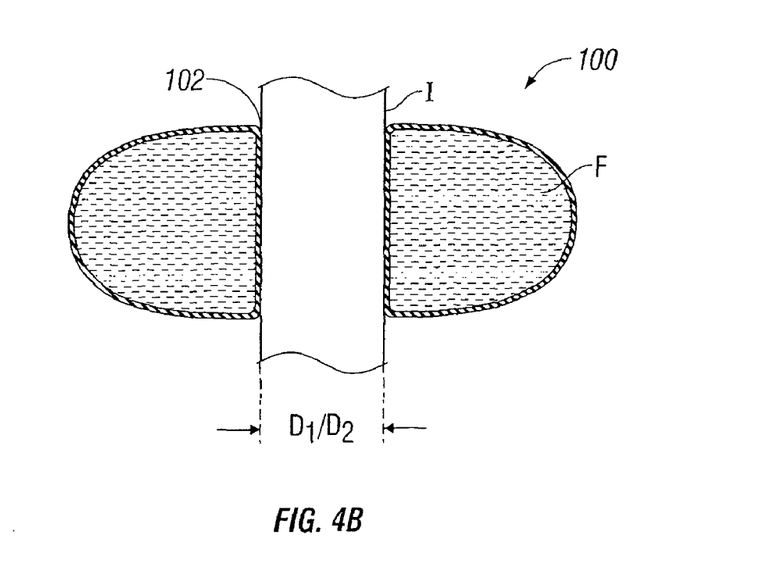
FIG. 4B is a side, cross-sectional view of the seal member of FIG. 4A shown in the subsequent condition.

Referring now to FIGS. 2A-5, seal member 100 includes an aperture 102 that is configured and dimensioned to removably receive a surgical object "I" (FIGS. 4A-4B). Seal member 100 may define a substantially torroidal configuration, as seen in FIGS. 2A-2B for example, or alternatively, seal member 100 may define a substantially conical configuration 101, as seen in FIG. 3A, that extends distally to thereby facilitate insertion of surgical object "I" within seal member 100. Seal member 100 further includes an internal cavity 104 that is defined between proximal and distal surfaces 106, 108, respectively. Cavity 104 is substantially annular in configuration in that cavity 104 circumscribes aperture 102. Cavity 104 may be defined during the formation of seal member 100, or subsequently thereafter, through any suitable method of manufacture, including but not being limited to casting, extrusion, drilling, molding, or milling. In one embodiment of seal member 100, internal cavity 104 is configured to retain a biocompatible fluid "F" therein, e.g., air, water, or saline, as seen in FIGS. 2A-2B and 4A-4B, for example. However, in an alternate embodiment, cavity 104 may be configured to house a plurality of bladders 110 that are each configured to retain fluid "F" therein such that bladders 110 may be inflated, as seen in FIG. 3B. Bladders 110 are connected through interstitial members 112 which are configured to facilitate fluid communication between bladders 110. Further details regarding bladder 110 may be obtained though reference to Provisional U.S. Patent Application Ser. No. 61/043,797 to Mozdzier et al.

Figure 5:
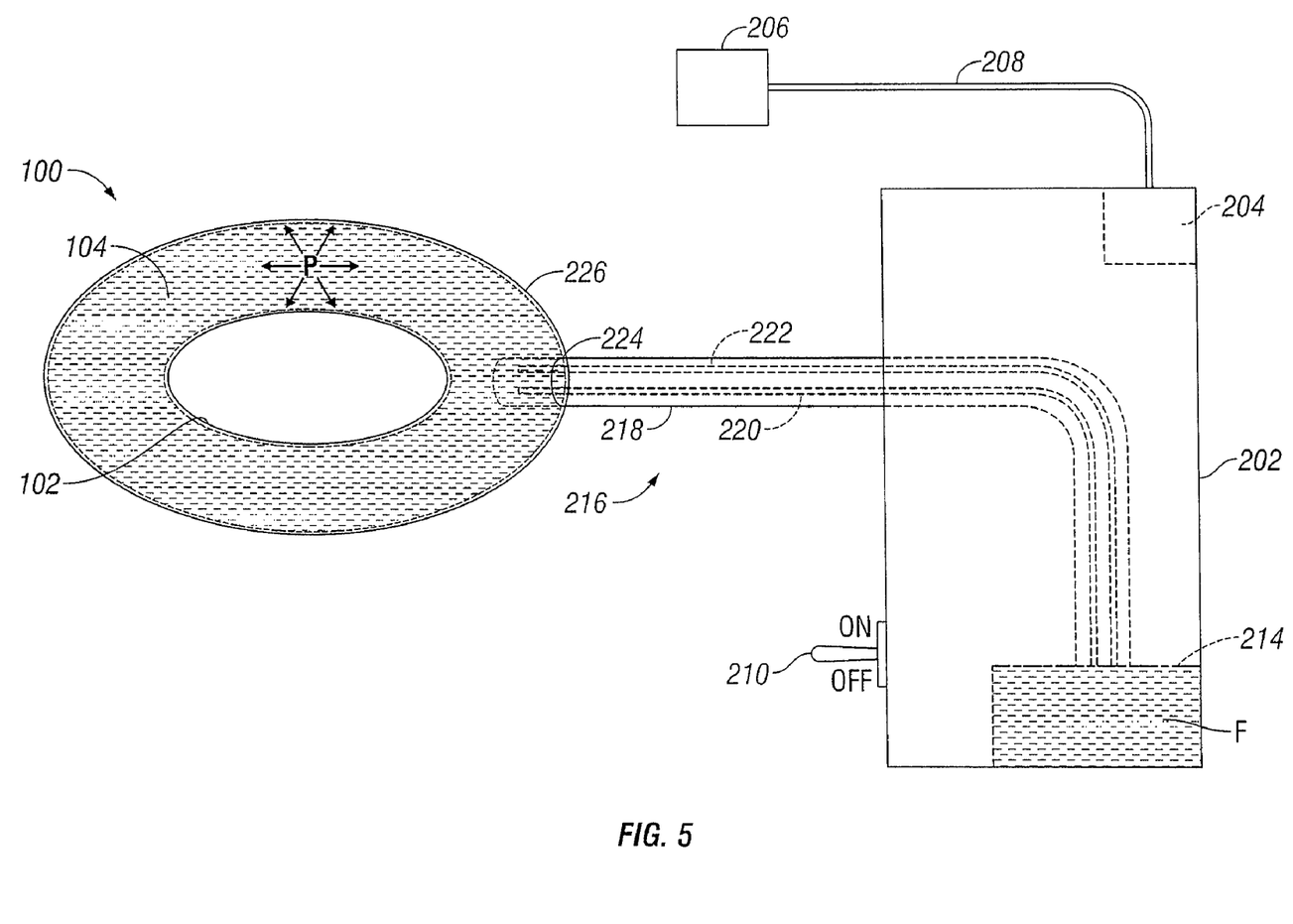
FIG. 5 is a partial, schematic view of the surgical access assembly of FIG. 1 illustrating the seal member in operative communication with the pump assembly.

Pump assembly 200 will now be described in detail with reference to FIG. 5. For the purposes of discussion, seal member 100 is shown as removed from housing 12 of surgical access assembly 10 (FIG. 1). Pump assembly 200 includes a pump member 202 that is in communication with seal member 100 to thereby circulate fluid "F" through seal member 100. Pump member 202 may be any structure or mechanism that is selectively activatable from an idle state to an activated state to thereby stream fluid "F" into and out of seal member 100. Pump member 202 includes a motor 204 operatively connected to a power source 206 through a cable member 208. Pump member 202 may be controlled through the use of an "on/off" mechanism, such as a switch or potentiometer 210, or alternatively, through the employ of one or more processing units 212 (FIGS. 6-8), as discussed herein below.

Fluid "F" is communicated from a reservoir 214 to seal member 100, and subsequently from seal member 100 to reservoir 214, through one or more conduits 216. Reservoir 214 may be disposed either within pump member 202, as shown in FIG. 5, or externally thereof. Conduit 216 may comprise a single tube 218 including respective upstream and downstream lumens 220, 222 each configured to permit fluid "F" to flow therethrough in a single corresponding direction only, or alternatively, conduit 216 may comprise individual upstream and downstream tubes (not show) each having a single lumen extending therethrough. Conduit 216 is connected to seal member 100 about an egress 224 formed therein that is configured to permit fluid "F" to pass therethrough such that fluid "F" may enter and exit seal member 100. As shown in FIG. 5, conduit 216 may be in direct fluid communication with internal cavity 104 such that fluid "F" may be circulated therethrough. Alternatively, however, in those embodiments of surgical access assembly 10 including the seal member 100 depicted FIG. 3B, egress 224 is in fluid communication with at least one bladder 110 or interstitial member 112. Egress 224 may be formed in periphery 226 of seal member 100 as shown in either proximal or distal surfaces 106, 108 thereof (FIG. 2B) or in any other suitable location.

As fluid "F" fills seal member 100, fluid "F" exerts radial pressure "P" outwardly therefrom. This pressure acts to close aperture 102, increasingly restricting the transverse dimension thereof, and thereby transitions seal member 100 from a first (or rest) condition (FIGS. 2A-2B) to a second (or restricted) condition (FIGS. 4A-4B). To allow seal member 100 to reversibly transition between the first condition and the at least one subsequent condition, seal member 100 is formed of a biocompatible material capable of resilient deformation.

In the first condition, aperture 102 defines a first dimension "$D_1$" measured along an axis B-B that extends in transverse relation to the longitudinal axis A-A. The first dimension "$D_1$" is appreciably larger than an outer dimension "$D_I$" of surgical object "I" such that surgical object "I" may be inserted into aperture 102 with little resistance. While the use of a surgical object "I" with an outer dimension lying generally within the range of approximately 5 mm to approximately 15 mm is conventional, the employ of substantially larger or smaller surgical objects in connection with surgical access assembly 10 (FIG. 1) is not beyond the scope of the present disclosure. When seal member 100 is in the at least one subsequent condition, aperture 102 defines a second transverse dimension "$D_2$" that is both smaller than the first transverse dimension "$D_1$" and typically less than the outer diameter "$D_I$" of surgical object "I". The deformable material comprising seal member 100 allows aperture 102 to stretch and thereby conform to the larger outer dimension "$D_I$" of surgical object "I", creating a substantially fluid-tight seal with surgical object "I" and curtailing the escape of insufflation gas through seal member 100.

It should be understood that the transverse dimension of aperture 102 may be controlled by adjusting the volume of fluid "F" retained within seal member 100. Accordingly, upon its departure from the first condition, seal member 100 may subsequently transition between a plurality of conditions in which aperture 102 defines either a smaller or larger transverse dimension, thereby allowing for the use of seal member 100 in connection with surgical objects of various sizes and dimensions.

Referring now to FIGS. 1-2B and 4A-5, the use and function of surgical access assembly 10 will be discussed. The target work site is first insufflated with a suitable biocompatible gas, e.g., $CO_2$ gas, such that a larger internal work space may be created within the patient, thereby providing greater access to internal organs, cavities, tissues, etc. The insufflation may be performed with an insufflation needle or similar device, as is conventional in the art. Following insufflation, surgical access assembly 10 is positioned such that access member 14 is placed within percutaneous access point 18 in the patient's tissue "T", either preexisting or created by the clinician using an obturator (not shown) or the like. Subsequently, surgical object "I" is inserted into surgical access assembly 10.

Initially, seal member 100 is in the first condition (FIGS. 2A-2B) such that surgical object "I" may be inserted into, and passed through, aperture 102 with little resistance. In one method of use, pump assembly 200 is activated either concomitantly with the introduction of surgical object "I", or subsequently thereafter, such that fluid "F" begins to fill seal member 100. As seal member 100 fills with fluid "F", seal member 100 transitions into the at least one subsequent condition (FIGS. 4A-4B), surrounding surgical object "I" such that a substantially fluid-tight seal is formed. In an alternate method of use, pump assembly 200 may be activated prior to the introduction of seal member 100 such that seal member 100 transitions into the at least one subsequent condition prior to the insertion of surgical object "I" into aperture 102. As discussed above, the dimensions of aperture 102 are smaller than outer dimension "$D_I$" of surgical object "I" in the at least one subsequent condition, thereby potentially inhibiting the distal advancement of surgical object "I" through seal member 100. To facilitate the advancement of surgical object "I", surgical access assembly 10 may provide for the incorporation of one or more lubricous fluids (not shown), as discussed in Provisional U.S. Patent Application Ser. No. 60/980,521 to Bettuchi et al., the entire contents of which are incorporated by reference herein. In this alternate method of use, as surgical object "I" is advanced distally through the restricted aperture 102 of seal member 100, surgical object "I" dilates aperture 102 such that the second transverse dimension "$D_2$" substantially approximates the outer dimension "$D_I$" of surgical object "I", thereby creating a substantially fluid-tight seal between seal member 100 and surgical object "I".

During the course of a minimally invasive procedure, it is often necessary for a clinician to manipulate surgical objects laterally so as to access particular regions of an insufflated work space. The incorporation of fluid "F" allows the seal formed between seal member 100 and surgical object "I" to be maintained during this manipulation, as discussed in Provisional U.S. Patent Application Ser. No. 61/043,797 to Mozdzier et al.

The pressure in seal member 100, and accordingly, the seal formed between seal member 100 and surgical object "I", may be maintained until such time that fluid "F" is communicated from seal member 100 and returned to reservoir 214. As seal member 100 is drained, seal member 100 returns to its first condition. During this transition, aperture 102 is enlarged, thereby facilitating the removal of surgical object "I" from seal member 100 will little resistance. Surgical access assembly 10 may then be removed from the access point 18 in the patient's tissue "T", and the access point 18 may be closed.

Figure 6:
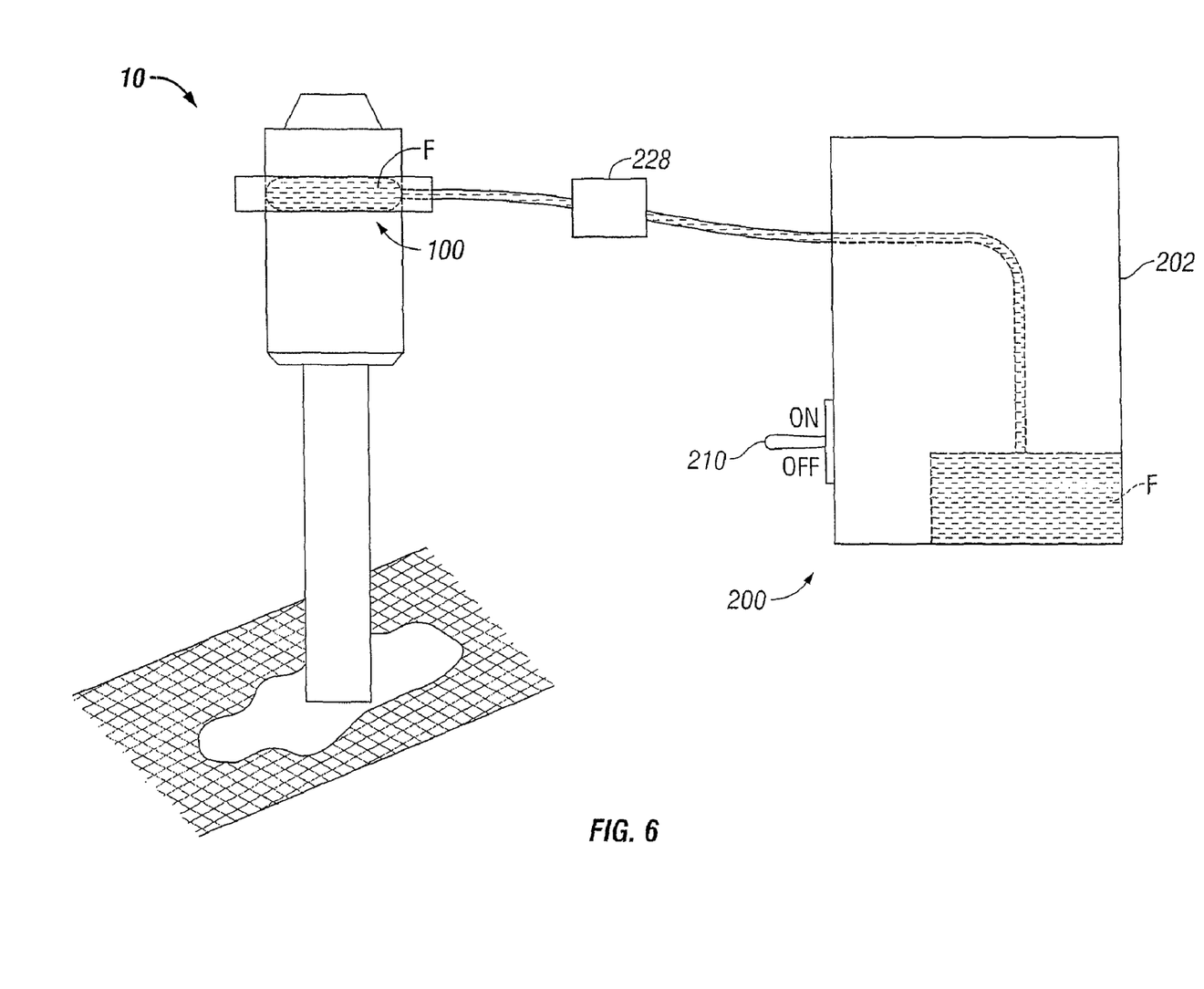
FIG. 6 is a side, schematic view of the surgical access assembly of FIG. 1 illustrating the seal member in operative communication with one embodiment of the pump assembly that further includes a pressure transducer.

Referring now to FIG. 6, in one embodiment of the surgical access assembly 10 disclosed herein, pump assembly 200 includes a pressure transducer 228 disposed between seal member 100 and pump member 202. Upon activation of pump member 202, i.e., when switch 210 is moved into the "on" position, pressure transducer 228 acts to monitor the pressure exerted by fluid "F" as it fills seal member 100. Transducer 228 translates the measured pressure into an electrical signal 230, which may be displayed as a pressure reading such that the clinician may regulate the amount of fluid "F" within seal member 100, and the corresponding pressure exerted thereby upon surgical object "I", by selectively pumping fluid "F" into and out of seal member 100.

Figure 7:
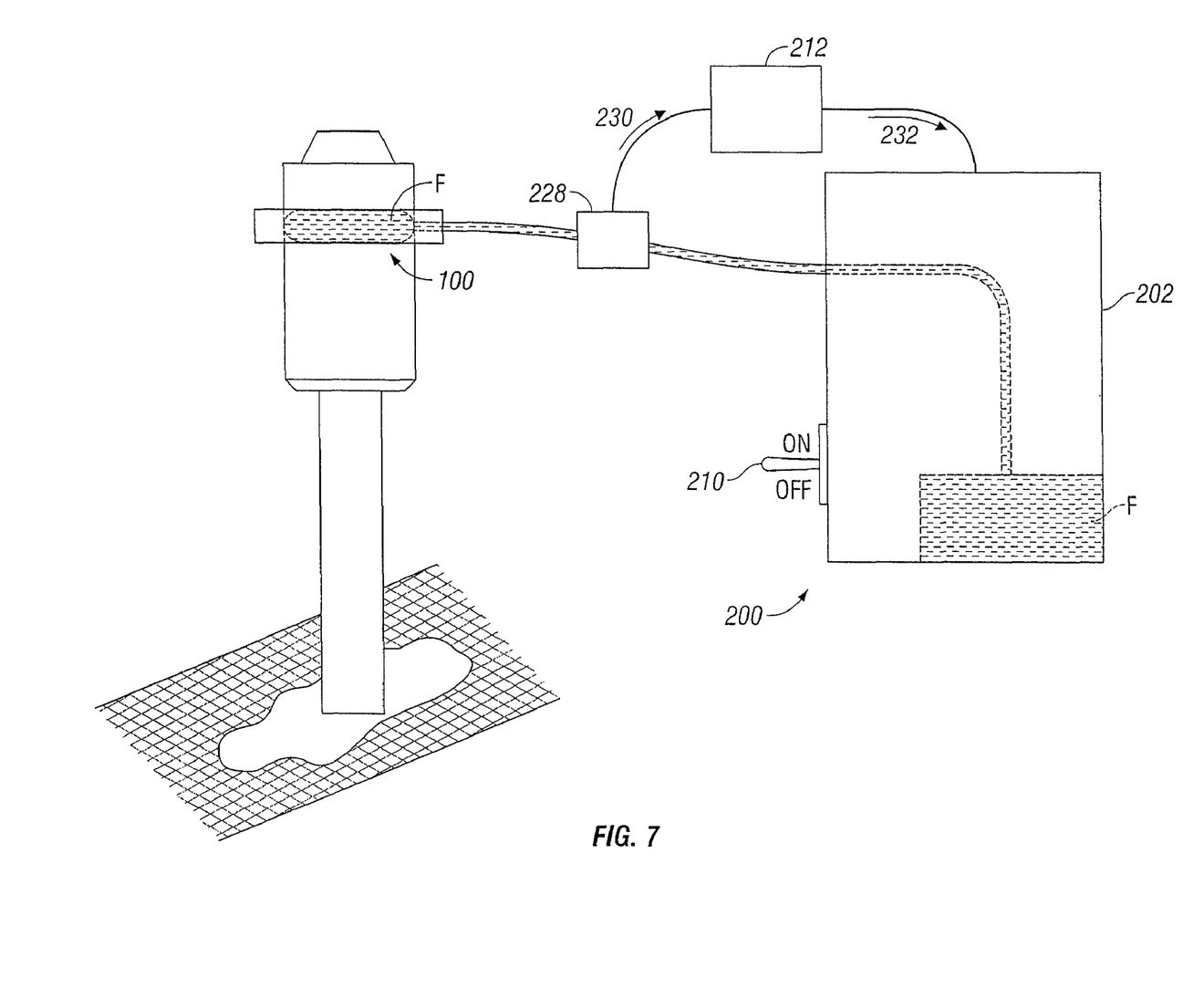
FIG. 7 is a side, schematic view of the surgical access assembly of FIG. 1 illustrating the seal member in operative communication with another embodiment of the pump assembly that includes a processing unit.

Alternatively, as seen in FIG. 7, the operation of pump assembly 200 may be controlled by processing unit 212 that is in communication with both pressure transducer 228 and pump member 202. In this embodiment, the pressure within seal member 100 measured by transducer 228 is communicated to processing unit 212 in the form of an electrical signal 230. Upon the receipt of signal 230, processing unit 212 utilizes a logic circuit (not shown) to determine whether a sufficient amount of fluid "F" is present within seal member 100 by comparing the measured pressure to a predetermined value stored within processing unit 212. Processing unit 212 then generates an electrical signal 232 which is subsequently communicated to pump member 202 to either adjust the pressure in seal member 100 by increasing or decreasing the volume of fluid "F" retained therein so as to achieve the predetermined value, or deactivate pump member 202 and thereby maintain the volume of fluid "F" and the corresponding pressure should the predetermined value be realized.

Figure 8:
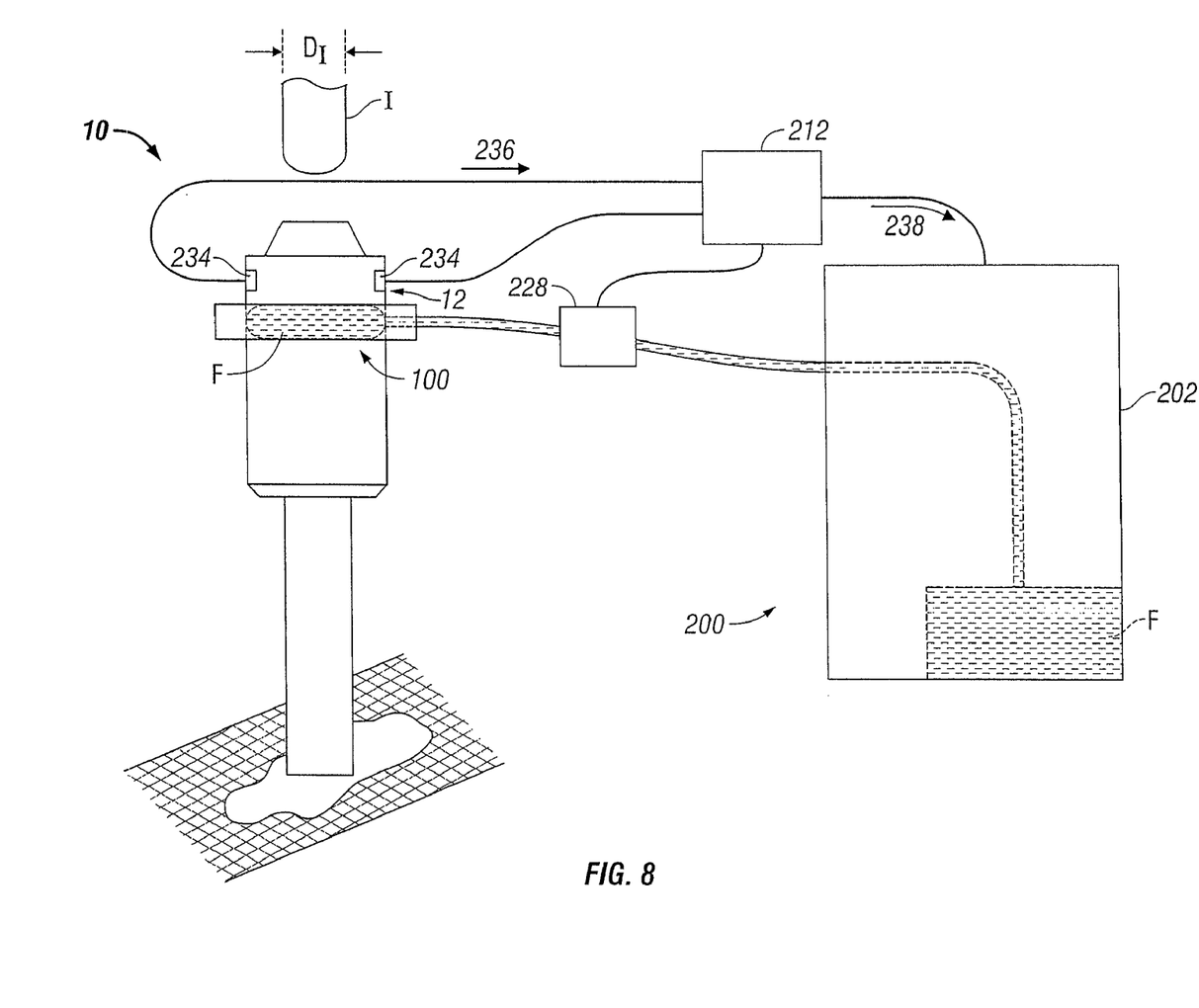
FIG. 8 is a side, schematic view of the surgical access assembly of FIG. 1 illustrating the seal member in operative communication with yet another embodiment of the pump assembly that further includes one or more sensors.

With reference now to FIG. 8, in another embodiment, pump assembly 200 may further include one or more sensors 234 disposed within housing 12, or at any other suitable location within or along surgical access assembly 10. In this embodiment, processing unit 212 is again in communication with both pump member 202 and transducer 228. However, processing unit 212 is also in communication with sensor 234. Sensor 234 is responsive to one or more attributes of surgical object "I", including but not being limited to its color, electrical impedance, magnetic impedance, or outer dimension "$D_I$", such that sensor 234 may be employed to detect the presence of surgical object "I" upon its introduction to housing 12. Upon detecting surgical object "I", sensor 234 generates an electrical signal 236 that is communicated to processing unit 212. Processing unit 212 subsequently interprets signal 236, again through the employ of its logic circuit (not shown), and generates a corresponding signal 238 that is communicated to pump member 202 to thereby begin the flow of fluid "F" into seal member 100. Thereafter, the clinician may regulate the pressure "P" (FIG. 5) within seal member 100 by controlling the flow of fluid "F" to and from seal member 100, as in the embodiment of FIG. 6, or alternatively, the pressure may be automatically regulated through the incorporation of pressure transducer 228, as discussed with respect to the embodiment of FIG. 7.

In the embodiment of FIG. 8, surgical access assembly 10 may include a delay mechanism (not shown) in communication with sensor 234 to provide a specified interval of time between the detection of surgical object "I" by sensor 234 and the subsequent activation of pump member 202. The incorporation of the delay mechanism prevents seal member 100 from transitioning into the at least one subsequent condition until after surgical object "I" has been inserted, thereby allowing for the insertion of surgical object "I" with little resistance.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical access assembly, which comprises:
a housing;
an elongate access member extending from the housing, the access member dimensioned for positioning within a patient's tissue and defining a passageway therethrough configured to removably receive a surgical object;
a seal member disposed within the housing and having an aperture defined therein and extending therethrough, the seal member being adapted to transition between a first condition, wherein the aperture includes a first transverse dimension, and at least one subsequent condition, wherein the aperture includes a second transverse dimension that is smaller than the first transverse dimension;
a pump assembly operatively coupled to the seal member and configured to circulate a fluid into and out of the seal member to thereby respectively transition the seal member between the first condition and the at least one subsequent condition, the pump assembly including:
a pressure transducer adapted to measure pressure exerted by the fluid within the seal member, the pressure transducer being adapted to translate the measured pressure into a first signal;
a processing unit operatively coupled to the pressure transducer, the processing unit being configured to receive and process the first signal into at least one additional signal to control circulation of the fluid into and out of the seal member; and
at least one sensor operatively coupled to the housing and in communication with the processing unit, the at least one sensor being adapted to detect at least one attribute of a surgical object upon the introduction into the surgical access assembly, the sensor being configured to generate a signal in response thereto to control the pump assembly; and
a delay mechanism in communication with the at least one sensor to provide a specified interval of time between detection of the surgical object and activation of the pump assembly in order to minimize force necessary to advance the surgical object through the seal member.

2. The surgical access assembly of claim 1, wherein the seal member is at least partially formed of a semi-resilient material that resiliently transitions between the first condition and the at least one subsequent condition upon activation of the pump assembly.

3. The surgical access assembly of claim 1, wherein the aperture defines a first transverse dimension when the seal member is in the first condition and a second transverse dimension when the seal member is in the at least one subsequent condition, the second transverse dimension being smaller than the first transverse dimension.

4. The surgical access assembly of claim 1, wherein the at least one subsequent condition includes a plurality of conditions in which the aperture defines an increasingly restricted transverse dimension.

5. The surgical access assembly of claim 3, wherein the first transverse dimension facilitates insertion of the surgical object into the aperture of the seal member.

6. The surgical access assembly of claim 3, wherein the second transverse dimension substantially approximates an outer dimension of a surgical object inserted through the aperture such that a substantially fluid-tight seal is formed therewith.

7. The surgical access assembly of claim 1, wherein the seal member includes at least one egress in operative communication with the pump assembly which is configured to permit circulation of the fluid into and out of the seal member.

8. The surgical access assembly of claim 7, wherein the pump assembly includes at least one pump member selectively activatable between an activated state and a deactivated state, the pump member circulating fluid into and out of the seal member when in the activated state.

9. The surgical access assembly of claim 8, wherein the pressure transducer is operatively coupled to the pump member.

10. The surgical access assembly of claim 9, wherein the processing unit is operatively coupled to the pump member, whereby the at least one additional signal is communicated to the pump member.

11. The surgical access assembly of claim 10, wherein the pump member includes a repositionable switch to transition the pump member between an activated and a deactivated state.

12. The surgical access assembly of claim 1, wherein the at least one sensor is configured, dimensioned, and adapted to detect one or more of the outer dimension, the color, the electrical impedance, and the magnetic impedance of the surgical object.

13. The surgical access assembly of claim 1, wherein the seal member includes an internal cavity defined therein.

14. The surgical access assembly of claim 13, wherein the fluid is retained within the internal cavity.

15. The surgical access assembly of claim 14, wherein the seal member further includes a plurality of bladder members disposed within the internal cavity, the plurality of bladder members being adapted to retain the fluid therein.

16. The surgical access assembly of claim 15, wherein each of the plurality of bladders resides in fluid communication with one another such that the fluid is circulated therebetween.

17. A surgical access assembly, which comprises:
   a housing configured and dimensioned for engagement with a patient's tissue;
   a seal member disposed within the housing and including an aperture extending therethrough, the seal member being configured and dimensioned to form a seal with an inserted surgical object;
   a pump assembly operatively coupled to the seal member and configured to circulate a fluid into and out of the seal member to facilitate reconfiguration of the aperture, the pump assembly including:
      a pressure transducer adapted to measure pressure exerted by the fluid within the seal member, the pressure transducer being adapted to translate the measured pressure into a first signal;
      a processing unit in communication with the pressure transducer, the processing unit being configured to receive and process the first signal into at least one additional signal to control circulation of the fluid into and out of the seal member; and
      at least one sensor in communication with the processing unit, the at least one sensor being configured, dimensioned, and adapted to detect at least one attribute of the surgical object upon introduction into the surgical access assembly, and generate a signal in response thereto to control the pump assembly; and
   a delay mechanism in communication with the at least one sensor to provide a specified interval of time between detection of the surgical object and activation of the pump assembly in order to minimize force necessary to advance the surgical object through the seal member.

18. The surgical access assembly of claim 17, wherein the at least one sensor is configured, dimensioned, and adapted to detect one or more of the outer dimension, the color, the electrical impedance, and the magnetic impedance of the surgical object.

19. The surgical access assembly of claim 17, further including an elongate member extending distally from the housing, the elongate member being configured and dimensioned for positioning within a percutaneous tissue tract to facilitate insertion of the surgical object into an internal surgical worksite.

* * * * *